(12) United States Patent
Rao et al.

(10) Patent No.: US 8,350,029 B2
(45) Date of Patent: Jan. 8, 2013

(54) PROCESS FOR THE PREPARATION OF GEFITINIB

(75) Inventors: Dharmaraj Ramachandra Rao, Maharashtra (IN); Rajendra Narayanrao Kankan, Maharashtra (IN); Srinivas Laxminarayan Pathi, Karnataka (IN)

(73) Assignee: CIPLA Limited, Mumbai (IN)

( * ) Notice: Subject to any disclaimer, the term of this patent is extended or adjusted under 35 U.S.C. 154(b) by 314 days.

(21) Appl. No.: 12/595,812

(22) PCT Filed: Apr. 16, 2008

(86) PCT No.: PCT/GB2008/001343
§ 371 (c)(1), (2), (4) Date: Dec. 4, 2009

(87) PCT Pub. No.: WO2008/125867
PCT Pub. Date: Oct. 23, 2008

(65) Prior Publication Data
US 2010/0137586 A1    Jun. 3, 2010

(30) Foreign Application Priority Data
Apr. 16, 2007   (IN) ............................ 745/MUM/2007

(51) Int. Cl.
*C07D 239/94* (2006.01)
(52) U.S. Cl. .................................................. 544/293
(58) Field of Classification Search .................. 544/293
See application file for complete search history.

(56) References Cited

U.S. PATENT DOCUMENTS
6,297,257 B1   10/2001  Napoletano et al.

FOREIGN PATENT DOCUMENTS

| EP | 1477481 A1 | 11/2004 |
|---|---|---|
| IN | 901/CHE/2006 | 6/2006 |
| IN | 903/CHE/2006 | 6/2006 |
| WO | 9633980 A1 | 10/1996 |
| WO | 2004024703 A1 | 3/2004 |
| WO | 2005023783 A1 | 3/2005 |
| WO | 2005070909 A1 | 8/2005 |
| WO | 2008125867 A2 | 10/2008 |
| WO | 2008125867 A3 | 10/2008 |

OTHER PUBLICATIONS

Foreign communication from the priority application—International Search Report and Written Opinion, PCT/GB2008/001343, Nov. 6, 2008, 17 pages.
Foreign communication from the priority application—International Preliminary Report on Patentability, PCT/GB2008/001343, Oct. 20, 2009, 8 pages.

Yuan, Li, et al., "Synthesis of 4-(3-chloro-4-fluorophenylamino)-7-methoxy-6-[3-(4-morpholinyl)propoxy]quinazoline (ZD1839)," Chinese Journal of Medicinal Chemistry, 2005, vol. 15., No. 1, pp. 39-41, XP008093836.
Levin, M., et al., "Iressa™ Oncolytic EGF Receptor Tyrosine Kinase Inhibitor," Drugs of the Future, 2002, vol. 27, No. 4, pp. 339-345, XP009023704.

*Primary Examiner* — Brian McDowell
(74) *Attorney, Agent, or Firm* — Conley Rose, P.C.; Rodney B. Carroll

(57) ABSTRACT

There is provided a compound of formula III, and a process for preparing a compound of formula V comprising converting a compound of formula III to the compound V, wherein X is fluoro, chloro, bromo or iodo.

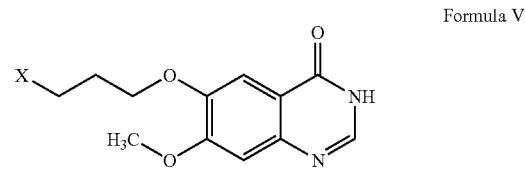

Formula V

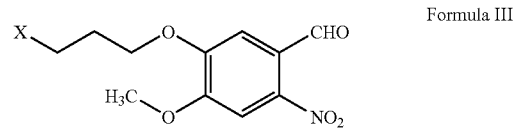

Formula III

There is also provided a process for preparing a compound of formula XI comprising converting a compound of formula X to the compound XI.

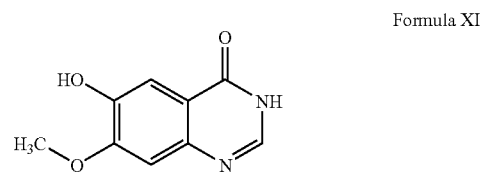

Formula XI

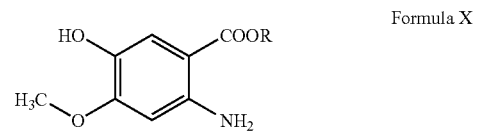

Formula X

The compounds V and XI so prepared may be used in a process for preparing gefitinib.

20 Claims, No Drawings

PROCESS FOR THE PREPARATION OF GEFITINIB

FIELD OF THE INVENTION

The present invention relates to a novel process for the preparation of gefitinib (formula I) and to novel intermediates which are produced during the course of carrying out the novel process.

BACKGROUND OF THE INVENTION

Gefitinib is an anilinoquinazoline which is useful in the treatment of a certain type of lung cancer (non-small cell lung cancer or NSCLC) that has not responded to chemotherapy. The chemical name for gefitinib is 4-(3'-chloro-4'-fluoroanilino)-7-methoxy-6-(3-morpholinopropoxy)quinazoline. Its structural formula is:

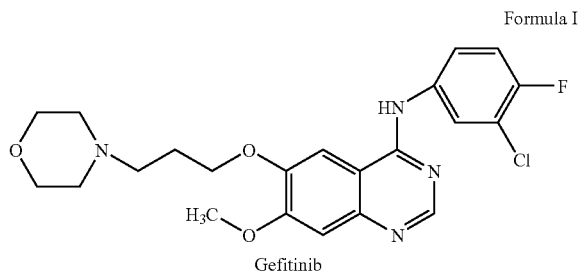 [SMILES: COc1cc2ncnc(Nc3ccc(F)c(Cl)c3)c2cc1OCCCN1CCOCC1]

Formula I

Gefitinib

The earliest known synthesis of gefitinib was first disclosed in the patent application WO 96/33980. The synthetic method employed is depicted in the following reaction scheme 1.

The process involves selective demethylation of 6,7-dimethoxy quinazoline-4-one using methanesutfonic acid and L-methionine to get its 6-hydroxyl derivative, which is protected by acetylation. The acetoxy compound is chlorinated and condensed with chloro-fluoroaniline. Hydrolysis of the acetoxy compound followed by etherification with 3-morpholinopropyl chloride gives crude gefitinib which is purified by column chromatography. The process suffers from many disadvantages as it involves several protection and deprotection steps. The selective demethylation using methionine results in isomeric impurities and has to be purified or else the impurity carries over to subsequent steps in the preparation of gefitinib making it more difficult to isolate a pure product. The process also leads to formation of an N-alkylated impurity at the final stage which must be separated by column chromatography to obtain gefitinib.

Several other approaches are also described in the literature to make gefitinib.

WO 2004/024703 discloses a process for the preparation of gefitinib starting from 3-hydroxy-4-methoxy benzonitrile which involves condensation of 3-hydroxy-4-methoxy benzonitrile with morpholino propyl chloride, nitration, reduction with sodium dithionite to amino compound, hydrolysis of nitrile to amide, cyclisation in the presence of formamide to obtain quinazoline, chlorination with phosphorous oxychloride and finally condensation with chloro-fluoro aniline to obtain gefitinib. The process involves multiple steps and hence is time consuming.

WO 2005/023783 discloses a process for the manufacture of gefitinib starting from 2-amino-4-methoxy-5-(3-morpholinopropoxy)benzonitrile. The process involves a rearrangement reaction of 3-(3-chloro-4-fluorophenyl)-7-methoxy-6-(3-morpholinopropoxy)3,4-dihydroqunazoline-4-

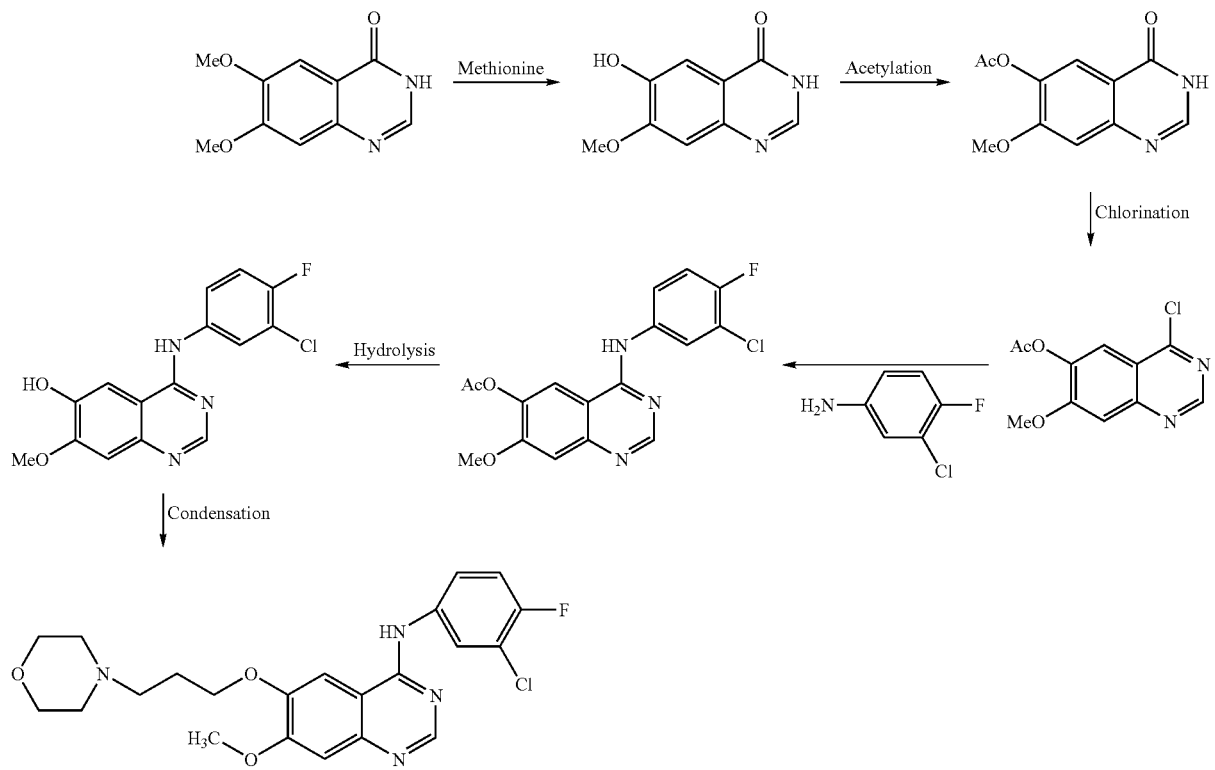

imine. The process is not feasible industrially, as the basic raw material is not readily available on a commercial scale and involves the use of excess 3-chloro-4-fluoroaniline which is expensive. A further draw back of the process is in the isomerization of the 4-imine compound which requires anhydrous conditions at high temperature for a longer duration of 96 hours. All the problems associated with this prior art process are overcome by the novel process of the present invention.

WO2005/070909 discloses a process for the preparation of gefitinib starting from isovanillin as depicted in scheme 2

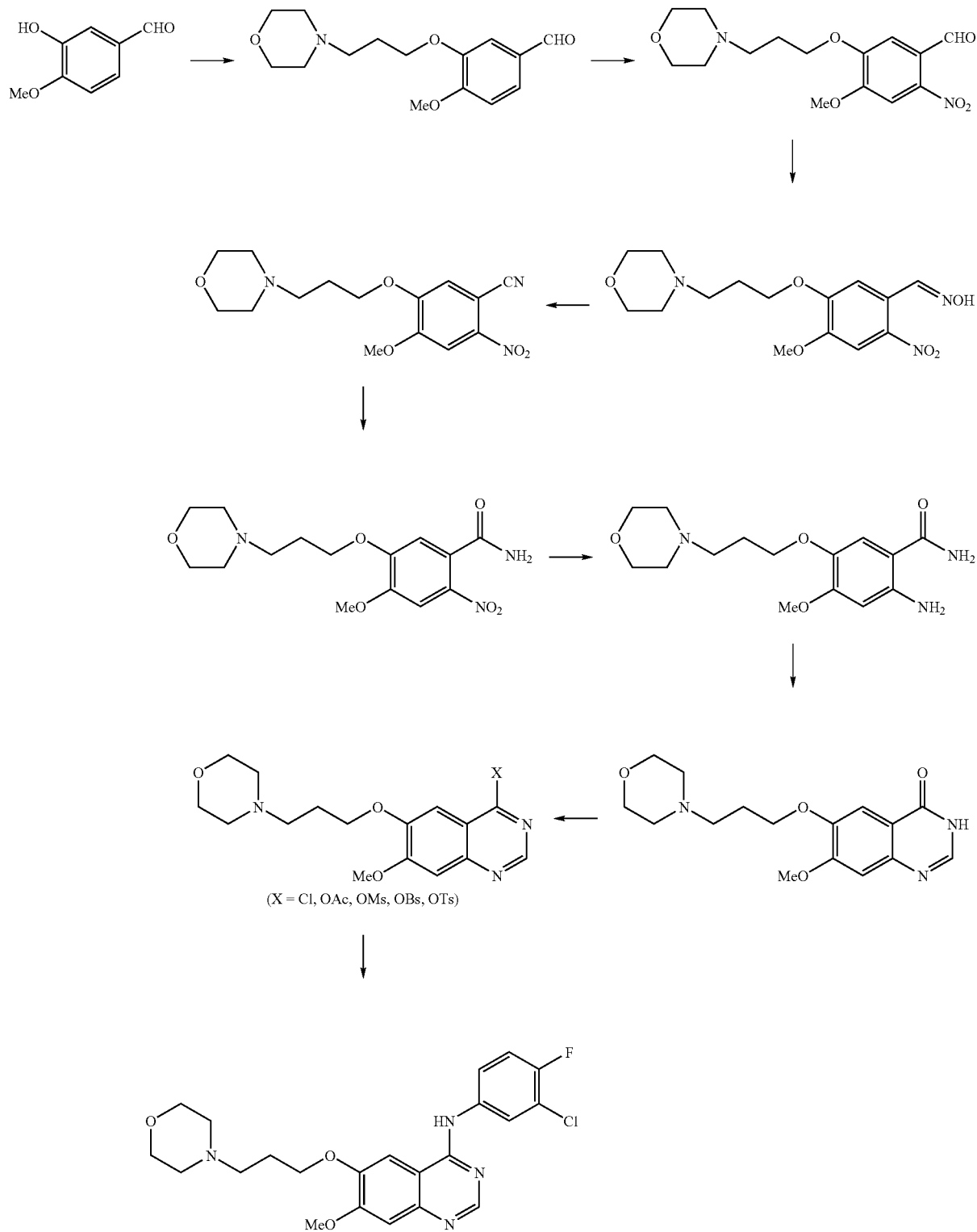

The WO' 909 process has disadvantages as it forms cis-trans geometrical isomers of the oxime, which have different reactivities. Furthermore, the process uses a large excess of acetic anhydride to convert the oxime to the nitrile at higher temperature.

The patent applications 901/CHE/2006 and 903/CHE/2006 disclose another route for preparing gefitinib starting from isovanillin. The process involves formation of a formamido compound [N'-[2-cyano-4-{3-(4-morpholinyl) propoxy}phenyl]-N,N-dimethyl formamide], which is unstable and may result in undesired impurities in the final condensation with 3-chloro-4-fluoro aniline, thereby making the process less feasible on an industrial scale.

The processes disclosed in the prior art are cumbersome. Therefore, there exists a need for a more economical and efficient method of making gefitinib which is suitable for industrial scale-up.

The process of the present invention avoids use of reagents such as sodium dithionite, acetic anhydride and allows substantial reduction in the number of problems associated with these reagents.

OBJECTS OF THE INVENTION

The object of the present invention is to provide an improved process for preparing gefitinib.

Yet another object of the present invention is to provide an improved process via new intermediates for the synthesis of gefitinib.

Yet another object of the present invention is to provide a process which is simple, economical and suitable for industrial scale-up.

STATEMENTS OF THE INVENTION

According to a first aspect of the present invention, there is provided a process for preparing a compound of formula V

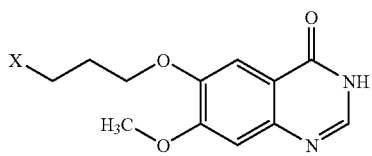

Formula V comprising converting a compound of formula III

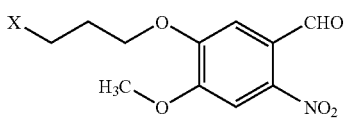

Formula III to the compound of formula V, wherein X is selected from fluoro, chloro, bromo or iodo. Preferably, X is chloro or bromo, most preferably chloro.

In an embodiment, the compound III is converted to the compound V via the intermediate compound of formula IV

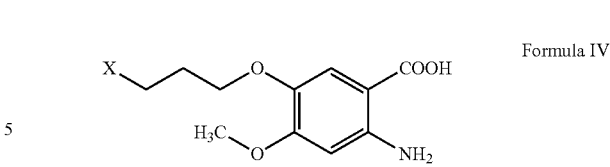

Formula IV wherein X is as defined above.

Compound III may be converted to compound IV by oxidation followed by nitro reduction.

The oxidation may involve reacting compound III with a base and a peroxide. The base may be an alcoholic NaOH solution. The alcohol may be methanol. The peroxide may be $H_2O_2$, for example an aqueous solution of $H_2O_2$. The pH of the reaction may be maintained at a pH of 10.5 to 11.5, for example by addition of further alcoholic NaOH solution. After reaction completion, the pH of the reaction mass may be adjusted to 2.0 to 3.0 using an acid such as hydrochloric acid. The oxidation may be carried out at a temperature ranging from 40 to 50° C., preferably 45° C.

The reduction involves hydrogen in the presence of a noble metal catalyst. A preferred noble metal catalyst is palladium. The source of hydrogen may be hydrogen gas or a hydrogen-donating compound such as ammonium formate or hydrazine hydrate. A suitable solvent, such as ethyl acetate, may be used for reduction using hydrogen gas. The reduction may be carried out at a temperature ranging from 30 to 45° C., preferably 35 to 40° C.

In an embodiment, the nitro reduction is carried out using a hydrogen-donating compound such as ammonium formate or hydrzine hydrate in the presence of hydrogen transfer catalysts.

Suitably, the hydrogen donating compound is hydrazine hydrate.

Suitably, the hydrogen transfer catalyst is selected from $FeCl_3.6H_2O$-activated carbon, Fe (III) oxide hydroxide or Fe (III) oxide, Zn—C, Fe—C, Pd—C, Pt—C, Raney Ni, graphite and clays.

In an embodiment, the nitro compound together with hydrazine hydrate is supported on a solid material such as alumina, silica gel or clay, and this provides a reduced reaction time, easier work-up procedure and enhanced selectivity and reactivity without racemization.

In an embodiment, the reduction is conducted in refluxing alcoholic solvents or dioxane. A suitable alcoholic solvent is methanol.

In another embodiment, the nitro reduction is carried out using ammonim formate and a hydrogenation-dehydrogenation catalyst in the presence of an inert solvent.

Suitably, the inert solvent employed is selected from alcohol solvents such as methanol, ethanol, isopropyl alcohol, butanol or polar aprotic solvents such as acetonitrile, DMF, DMSO or THF.

Suitably, the hydrogenation-dehydrogenation catalyst comprises a noble metal catalyst such as palladium, ruthenium or rhodium supported on carbon, clay, silica or alumina.

In this embodiment, the reduction is carried out at a temperature ranging from about 25° C. to about the reflux temperature of the solvent used.

Compound IV may be converted to compound V by the Niementowski synthesis. This synthesis is well known to those skilled in the art. The synthesis may involve reaction of compound IV with $HCONH_2$ and ammonium formate. The temperature of the reaction mass may range from 160 to 190° C., preferably from 170 to 180° C. After reaction completion, the temperature of the reaction mass may be reduced and the product isolated, for example by filtration and drying under vacuum.

According to another aspect of the present invention, there is provided a process for preparing gefitinib of formula I

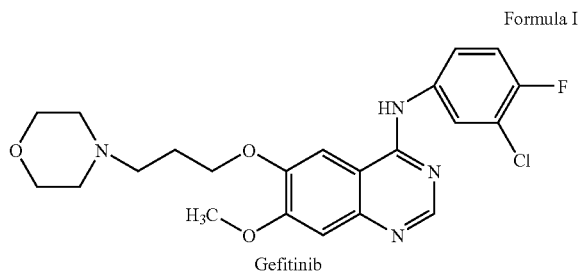 [SMILES: COc1cc2ncnc(Nc3ccc(F)c(Cl)c3)c2cc1OCCCN1CCOCC1]
Gefitinib comprising converting a compound of formula V to gefitinib, wherein the compound V has been prepared by a process as described above.

The conversion may be carried out by any suitable process. In an embodiment, the conversion comprises chlorinating the compound V to produce a compound of formula VI

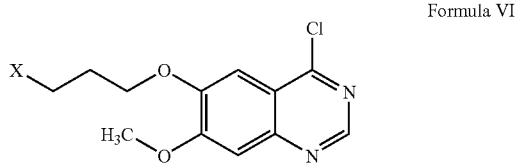

wherein X is as defined above.

The conversion to gefitinib may further comprise reacting the compound VI with morpholine to produce compound VII

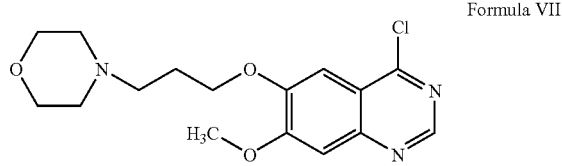 [SMILES: COc1cc2ncnc(Cl)c2cc1OCCCN1CCOCC1]

The conversion to gefitinib may further comprise condensing compound VII with 3-chloro-4-fluoroaniline.

The process of the present invention is advantageous as the process for preparing intermediate III does not involve the use of an oxime compound, nor the conversion of an oxime compound to a nitrile compound. By contrast, in WO2005/070909 (see Scheme 2 above), there is disclosed a process for preparing an intermediate in the synthesis of gefitinib, which process involves the formation of an oxime and conversion of the oxime to a nitrile. This has disadvantages as it forms cis-trans geometrical isomers of the oxime which leads to poor yield at the oxime stage. Furthermore, these isomers have different reactivities, which affects the rate of reaction at the nitrile stage. Still further, conversion of the oxime to the nitrile is not suitable industrially as the reaction is carried out at a high temperature of 120-125° C. using at least 5.4 times of acetic anhydride.

Another advantage of the process of the present invention is that it involves the use of compounds III and V which do not have a morpholinyl moiety. This is advantageous as 3-morpholino propyl halide is a more expensive reagent compared to compound II of the present invention. The process of WO2008/070909 involves the use of 3-morpholino propyl halide. The process of the present invention for preparing gefitinib is more economical than that of WO2005/07090 as the former uses morpholine towards the end of the process for which is less expensive.

According to another aspect of the present invention, there is provided a compound of formula III

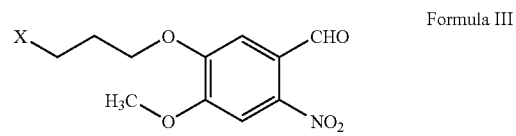

wherein X is selected from fluoro, chloro, bromo or iodo. Preferably, X is chloro or bromo, most preferably chloro.

According to another aspect of the present invention, there is provided a process for preparing a compound of formula III comprising converting a compound of formula II

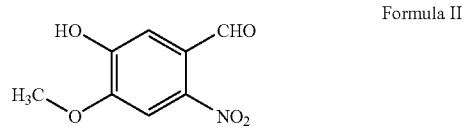

to the compound III. The conversion may involve reacting compound II with a compound of formula $X(CH_2)_3X$, wherein each X is independently selected from fluoro, chloro, bromo or iodo. In an embodiment, one X is chloro and the other X is bromo. The conversion may be carried out in the presence of a suitable solvent such as acetonitrile and a base such as $K_2CO_3$. The reaction mass may be extracted for example with water and methylene chloride.

Compound II may be prepared by nitrating isovanillin. This step is disclosed in U.S. Pat. No. 6,297,257 and may be carried out in accordance with the process disclosed therein.

According to yet another aspect of the present invention, there is provided a process for preparing a compound of formula XI

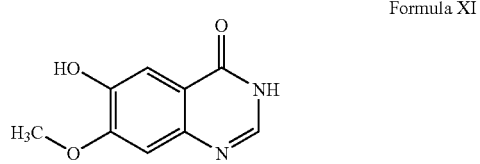

comprising converting a compound of formula X

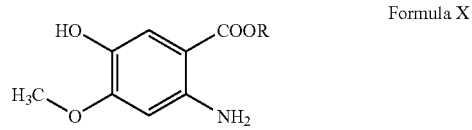

to the compound XI. In an embodiment, the conversion takes place in the presence of formic acid, or a reactive derivative thereof. The formic acid derivative may be formamidine acetate. The process may be carried out in a suitable solvent, such as methanol.

In an embodiment, the compound X is prepared by reducing a compound of formula IX

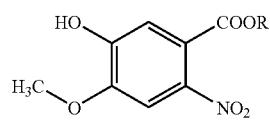

Formula IX to the compound X. The reduction may involve hydrogenation using Pd/C. The hydrogenation may be carried out in the presence of a suitable solvent such as ethyl acetate.

In an embodiment, the compound IX may be prepared by nitrating a compound of formula VIII

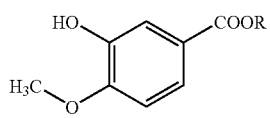

Formula VIII

The nitration may involve the use of an acid, such as acetic acid, and nitric acid. The reaction mass may be extracted, for example with water and methylene chloride.

The compound VIII may be prepared by oxidising isovanillin, followed by esterification.

The oxidation may involve reacting isovanillin with a base and a peroxide. The base may be an alcoholic NaOH solution. The alcohol may be methanol. The peroxide may be $H_2O_2$, for example an aqueous solution of $H_2O_2$. The pH of the reaction may be maintained at a pH of 10.0 to 12.0, preferably 10.5 to 11.5, for example by addition of further alcoholic NaOH solution. After reaction completion, the pH of the reaction mass may be adjusted to 2.0 to 3.0 using an acid such as hydrochloric acid. The oxidation may be carried out at a temperature ranging from 40 to 50° C., preferably 45° C.

The esterification may involve reacting the oxidised product with an alcoholic acid solution. The acid may be hydrochloric acid and the alcohol may be methanol. The reaction mass may be extracted with water and methylene chloride.

The process of the present invention for preparing compound XI, reduces or substantially elimiates isomeric impurities. In contrast, WO9633980 discloses a process in which 6,7-dimethoxy-3,4-dihydroquinazolin-4-one is demethylated using methionine to prepare a compound of formula XI. The reaction is carried out at high temperature (above 200° C.) and is not selective, thus it results in formation of 10-15% of the isomeric impurity 6-hydroxy-7-methoxy-3,4-dihydroquinazolin-4-one and 10-15% of 6,7-dihydroxy-3,4-dihydroquinazolin-4-one (the desdimethylated compound). Hence, the WO9633980 process requires purification of intermediate XI; otherwise, these impurities carry over to subsequent steps.

According to a still further aspect of the present invention, there is provided a process for preparing gefitinib comprising converting a compound of formula XI to gefitinib, wherein the compound XI has been prepared according to a process as defined above.

The conversion to gefitinib may be carried out in accordance with the process described in WO9633960.

In an embodiment, the conversion to gefitinib comprises acetylating the compound XI to obtain 6-acetoxy-7-methoxy-quinazoline of the formula XII;

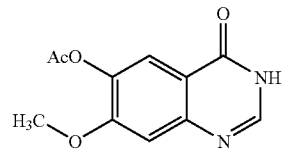

Formula XII chlorinating the 6-acetoxy-7-methoxy-quinazoline compound XII to obtain 6-acetoxy-4-chloro-7-methoxyquinazoline of formula XIII;

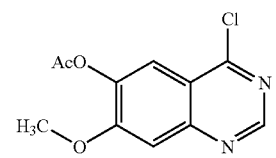

Formula XIII condensing the acetoxy compound XIII with 3-chloro-4-fluoro aniline to obtain 6-acetoxy-4-(3'-chloro-4'-fluoroanilino)-7-methoxyquinazoline of the formula XIV;

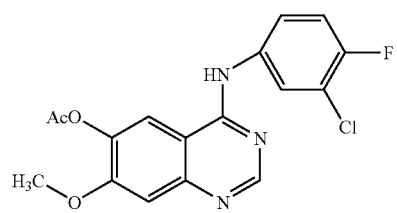

Formula XIV hydrolyzing the compound XIV by conventional methods to obtain 4-(3'-chloro-4'-fluoro-anilino)-6-hydroxy-7-methoxyquinazoline of the formula XV;

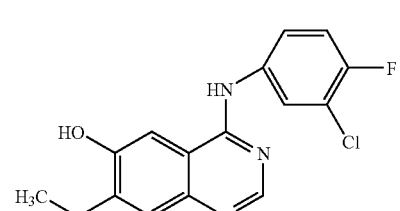

Formula XV and coupling 4-(3'-chloro-4'-fluoro-anilino)-6-hydroxy-7-methoxyquinazoline compound formula XV with a 3-morpholinopropane derivative of the formula XVI

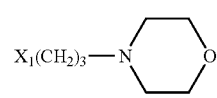

Formula XVI wherein $X_1$ is a displaceable group, in the presence of a base to obtain gefitinib of the formula I.

The present invention also provides compounds III, V and IX prepared according to any one of the processes described above. Further, the present invention provides gefitinib prepared according to any one of the processes described above. The gefitinib so prepared may be formulated with one or more pharmaceutically acceptable excipients to provide a pharmaceutical composition. Such excipients and compositions are well known to those skilled in the art.

The invention is hereinafter detailed in greater details, no part of which may be construed as restrictive to the scope of the instant invention.

DETAILED DESCRIPTION OF THE INVENTION

In an embodiment of the present invention, there is provided an improved synthesis of gefitinib from isovanillin, as depicted below in reaction scheme 3.

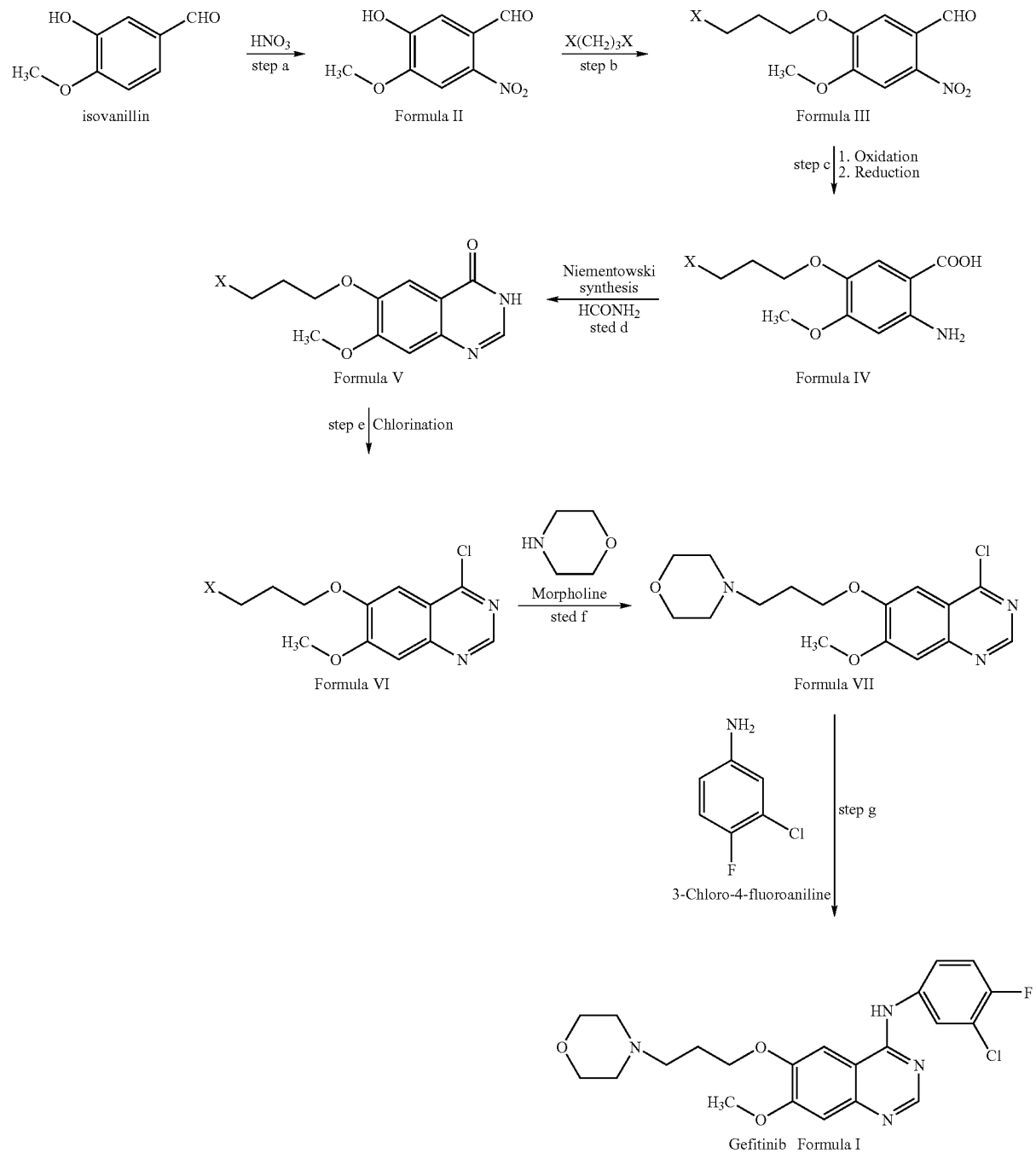

Where X = Cl, Br, I

Accordingly, in an embodiment, the present invention provides a process for the preparation of gefitinib of formula I, comprising:
nitrating isovanillin i.e 3-hydroxy-4-methoxy benzaldehyde of the formula:

isovaillin to obtain an intermediate, 5-nitro isovanillin of the formula II:

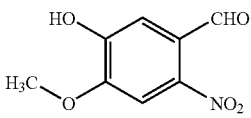

Formula II reacting the compound of formula II with compound X(CH$_2$)$_3$X, wherein each X is independently a fluorine, chlorine, bromine or iodine atom, preferably chlorine or bromine, in the presence of a base to yield a compound 3-(3-halopropoxy)-4-methoxy-6-nitro benzaldehyde of the formula III:

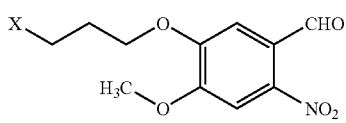

Formula III wherein X is as defined above;
oxidizing the 3-(3-halopropoxy)-4-methoxy-2-nitro-benzaldehyde of the formula III to the corresponding carboxylic acid and reducing the nitro group to obtain compound 2-amino-4-methoxy-5-(3-halopropoxy)benzoic acid of the formula IV:

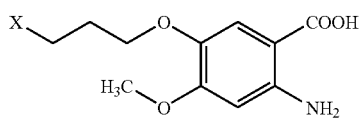

Formula IV wherein X is as defined above;

cyclizing the compound 2-amino-4-methoxy-5-(3-halopropoxy) benzoic acid of the formula IV using formic acid or a reactive derivative thereof to obtain 6-(3-halopropoxy)-7-methoxy-3H-quinazoline-4-one of the formula V:

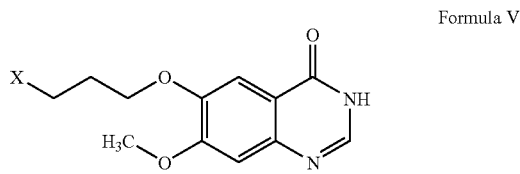

Formula V wherein X is as defined above;
chlorinating, 6-(3-halopropoxy)-7-methoxy-3H-quinazoline-4-one of the formula V to obtain an intermediate, 4-chloro-6-(3-halopropoxy)-7-methoxy-quinazoline of the formula VI:

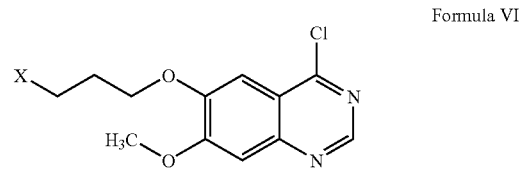

Formula VI wherein X is as defined above;
condensing, the intermediate of formula VI with morpholine to obtain 4-chloro-7-methoxy-6-(3-morpholino propoxy) quinazoline of the formula VII:

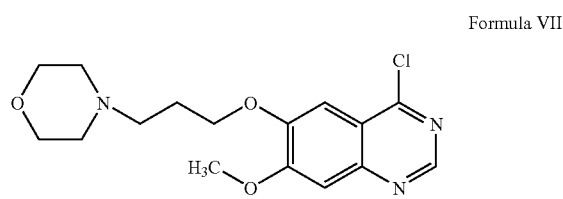 [SMILES: COc1cc2ncnc(Cl)c2cc1OCCCN1CCOCC1]

Formula VII condensing, 4-chloro-7-methoxy-6-(3-morpholino propoxy) quinazoline of the formula VII with 3-chloro-4-fluoroaniline to obtain gefitinib of formula I.
An alternate route for the synthesis of gefitinib from isovanillin according to the present invention is depicted below in reaction scheme 4.

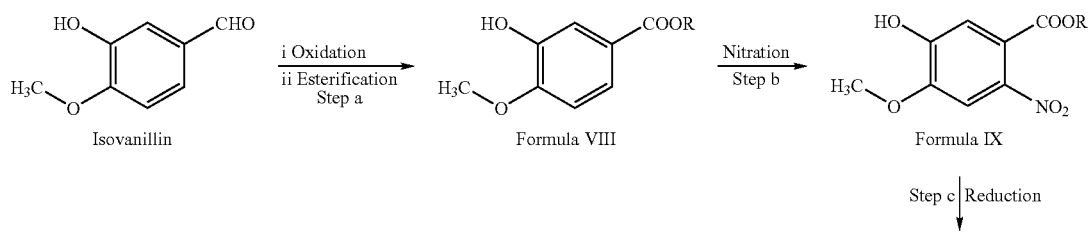

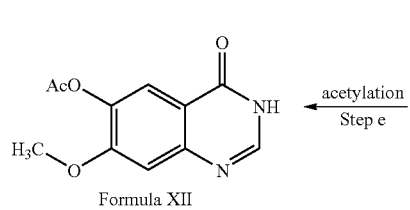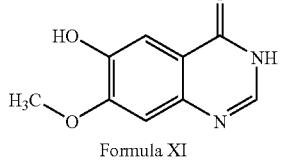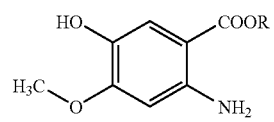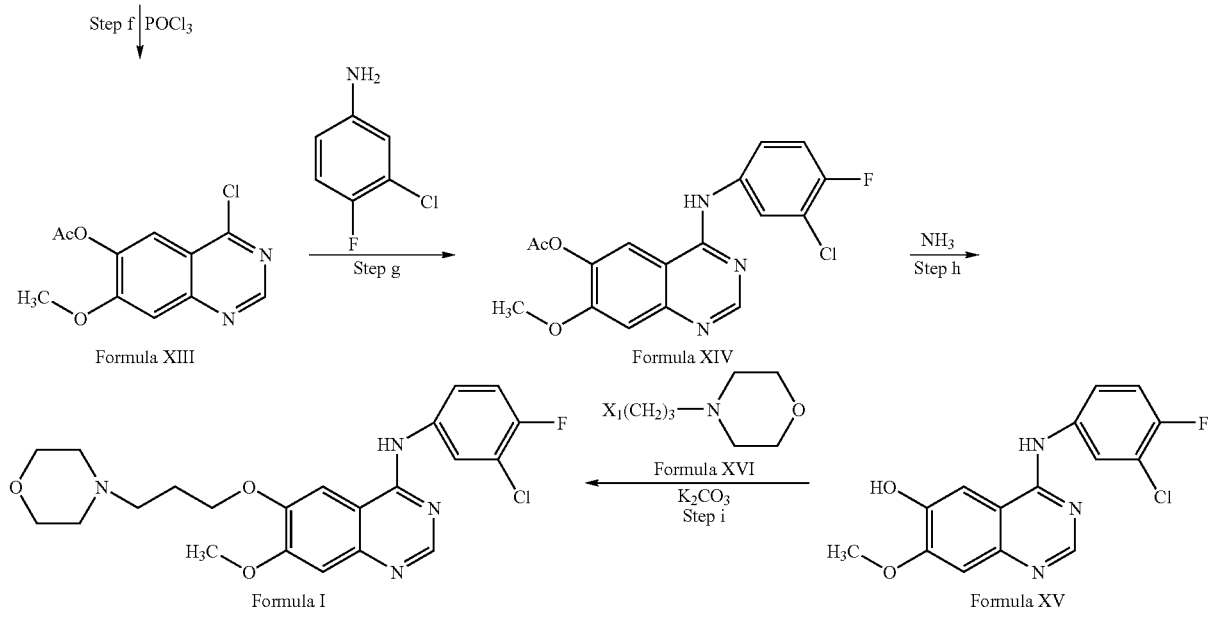

Accordingly, in an embodiment, the invention provides an improved process for the preparation of gefitinib of the formula I which comprises:

oxidizing isovanillin to the corresponding carboxylic acid and subsequently esterifying the acid to obtain a compound of the formula VIII

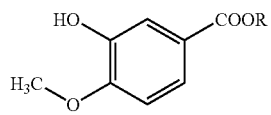

Formula VIII wherein R is an alkyl group;

nitrating the compound of formula VIII using a nitrating reagent to obtain a nitro intermediate of the formula IX

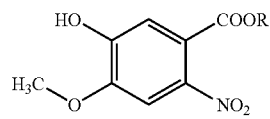

Formula IX wherein R is as described above;

reducing the nitro compound of formula IX to obtain an anilino compound of the formula X:

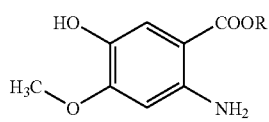

Formula X wherein R is as described above;

cyclizing the anilino compound of formula X with formic acid, or a reactive derivative thereof to obtain intermediate quinazoline of the formula XI;

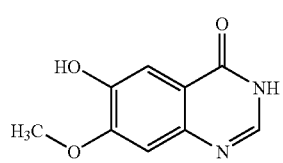

Formula XI acetylating the quinazoline of formula XI to obtain 6-acetoxy-7-methoxy-quinazoline of the formula XII;

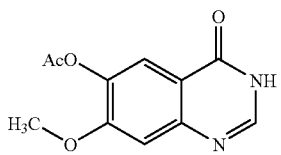

Formula XII chlorinating the 6-acetoxy-7-methoxy-quinazoline of formula XII to obtain an intermediate, 6-acetoxy-4-chloro-7-methoxyquinazoline of formula XIII;

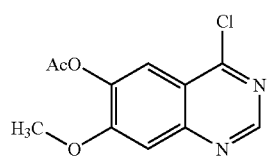

Formula XIII condensing the acetoxy compound of Formula XIII with 3-chloro-4-fluoro aniline to obtain 6-acetoxy-4-(3'-chloro-4'-fluoro-anilino)-7-methoxyquinazoline of the formula XIV;

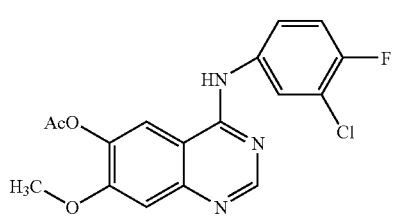

Formula XIV hydrolyzing the compound of formula XIV by conventional methods to obtain 4-(3'-chloro-4'-fluoro-anilino)-6-hydroxy-7-methoxyquinazoline of the formula XV;

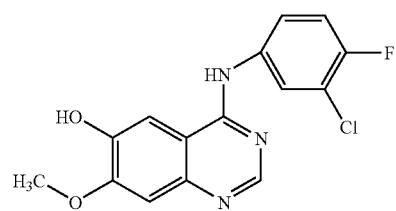

Formula XV and
coupling 4-(3'-chloro-4'-fluoro-anilino)-6-hydroxy-7-methoxyquinazoline of the formula XV with 3-morpholinopropane derivative of the formula XVI

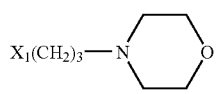

Formula XVI wherein $X_1$ is a displaceable group in the presence of a base to obtain gefitinib of the formula I.

Gefitinib obtained according to the process of the present invention, for example by following scheme 3 or 4, may be further purified by acid/base treatment or by crystallization from solvents to obtain pharmaceutically acceptable grade gefitinib of formula I.

Gefitinib was prepared by following the process of the present invention, using appropriate solvents, reagents and reaction conditions.

The details the invention given in the following examples, which are provided below for illustration only, and therefore these examples should not be construed to limit the scope of the invention.

EXAMPLE 1

Preparation of 4-(3'-chloro-4'-fluoroanilino)-7-methoxy-6-(3-morpholinopropoxy)-quinazoline (gefitinib) (Formula I)

Methanol (1200 ml) and 6-(3-morpholino propoxy)-7-methoxy-4-chloro quinazoline (200 gm) were stirred for 15 minutes at 25-30° C., then a solution of 4-fluoro-3-chloroaniline in methanol (213 gm in 400 ml) was charged and refluxed for 6 hours. The reaction mass was cooled to 15-20° C., hydrochloric acid (40 ml) was added drop wise, and stirred at 5-10° C. for 30 minutes. The solid obtained was filtered and washed with chilled methanol (150 ml). The solid was dissolved in a mixture of toluene (30 volume) and methanol (5 volume), the reaction mass was concentrated to half the volume and cooled to 5-10° C. The solid obtained was filtered, washed with toluene (200 ml) and dried at 45-50° C. to yield the title compound (183 gm, 70% yield).

EXAMPLE 2

Preparation of 6-(3-morpholino propoxy)-7-methoxy-4-chloroquinazoline (Formula VII)

DMF (3 lt), 6-(3-chloropropoxy)-7-methoxy-4-chloro quinazoline (200 gm) and morpholine (210 gm), were heated to 70-75° C. for 6-8 hours. The reaction mass was cooled to room temperature, and methylene chloride (2.5 lt) and water (2.5 lt) were charged. The layers separated and the aqueous layer extracted with methylene chloride twice (500 ml). The combined methylene chloride layer was washed with water, dried over sodium sulphate (10 gm) and concentrated completely at 35-40° C. to yield the title compound (200 gm, 85% yield).

EXAMPLE 3

Preparation of 6-(3-chloropropoxy)-7-methoxy-4-chloroquinazoline (Formula VI)

6-(3-chloropropoxy)-7-methoxyquinazoline-4-one (400 gm), thionyl chloride (3.2 lt) and DMF (100 ml) were refluxed for 7-8 hours. Thionyl chloride was distilled off completely under reduced pressure below 45° C. Methylene chloride (2.5 lt) and water (1.5 lt) were charged, stirred for 30 minutes at room temperature and the layers separated. The aqueous layer was extracted twice with methylene chloride (500 ml), the combined methylene chloride layer was washed with 1% sodium bicarbonate solution (1 lt), dried over sodium sulphate (20 gm) and concentrated under reduced pressure at 35-40° C. The residue was stirred with isopropyl alcohol (400 ml) at 40-45° C. for 1 hour, cooled to 0-5° C., the solids

EXAMPLE 4

Preparation of 6-(3-chloropropoxy)-7-methoxyquinazoline-4-one (Formula V)

2-amino-4-methoxy-5-(3-chloropropoxy)benzoic acid (450 gm), formamide (2250 ml) and ammonium formate (200 gm) were heated to 170-180° C. for 3-4 hours. The reaction mass was concentrated under reduced pressure at 140-150° C. The residue was stirred in methanol (1000 ml) at 45-50° C. and cooled to 5-10° C. The solid obtained was filtered to yield the title compound (420 gm, 90% yield).

EXAMPLE 5

Preparation of 2-amino-4-methoxy-5-(3-chloropropoxy)benzoic acid (Formula IV)

a) Preparation of 3-(3-chloropropoxy)-4-methoxy-6-nitrobenzoic acid

Methanol (4 lt), 3-(3-chloropropoxy)-4-methoxy-6-nitro benzaldehyde (560 gm) and 30% methanolic NaOH solution (5 ml) were heated to 45° C. To this reaction mass 35% of $H_2O_2$ solution (1200 ml) was added drop wise in 3-4 hours maintaining a pH of 10.5-11.5 with 30% methanolic NaOH solution. The reaction mass was quenched into ice water (10 kg) and the pH adjusted to 2.0-3.0 using hydrochloric acid. The solid obtained was filtered, washed with 50% aqueous methanol (500 ml) and dried at 45-50° C. to yield the title compound (510 gm, 86% yield).

bi) Preparation of 2-amino-4-methoxy-5-(3-chloropropoxy)benzoic acid—Using Hydrogen Gas Ethyl acetate (3 lt), Pd/C (50 gm) and 3-(3-chloropropoxy)-4-methoxy-6-nitrobenzoic acid (500 gm) were hydrogenated under a hydrogen pressure of 5-6 kg at 35-40° C. for 3-4 hours. The reaction mass was filtered and the clear filtrate was distilled under reduced pressure at 45-50° C. To the residue, hexane (1 lt) was charged, stirred at room temperature, the solids filtered and dried at 45-50° C. to yield the title compound (403 gm, 90% yield).

(bii) Preparation of 2-amino-4methoxy-5-(3-chloropropoxy)benzoic acid—Using Hydrazine Hydrate 3-(3-chloropropoxy)-4-methoxy-6-nitrobenzoic acid (100 gm), hydrazine hydrate (50 gms), neutral alumina (20 gms), charcoal (10 gms), water (50 ml) and methanol (500 ml) were mixed together. The reaction mass was heated to 50° C. A solution of ferric chloride (2 gms, 0.012M) in 50 ml methanol was introduced slowly at 55-60° C. The reaction mass was filtered over hyflo and the clear filtrate evaporated. The residue obtained was dissolved in 1.0-lit ethyl acetate, washed organic extract with water, evaporated to obtain title compound. (75 gms, 83.6%)

(biii) Preparation of 2-amino-4-methoxy-5-(3-chloropropoxy)benzoic acid—Using Ammonium Formate 3-(3-chloropropoxy)-4-methoxy-6-nitro benzoic acid (165 gms), 5% Paladium on carbon (16.5 gms) and DMF (0.66 lit) were mixed together. The reaction mass was heated to 40° C. Ammonium formate (82.5 gms) was charged in lots maintaining temperature below 50° C. The temperature of reaction mass slowly raised to 70° C. and maintained for 2 hours. The reaction mass was cooled to 30° C. and catalyst was removed by filtration and the clear filtrate evaporated. The residue was dissolved in ethyl acetate (0.825 lit), washed with water and evaporated to yield the title compound. (125 gms, 84.5%)

EXAMPLE 6

Preparation of 3-(3-chloropropoxy)-4-methoxy-6-nitro benzaldehyde (Formula III)

5-nitro isovanillin (500 gm), acetonitrile (3.5 lts), $K_2CO_3$ (750 gm) and chlorobromopropane (780 gm) were refluxed for 4 hours. The reaction mass was filtered hot, washed with acetonitrile (1 lt) and the filtrate was distilled off to remove solvent. The residue was dissolved in methylene chloride (4 lt) and washed with water. Water (3 lt) was charged to the methylene chloride layer, the pH adjusted to 7.0 to 7.5 with acetic acid, the methylene chloride layer separated, dried over sodium sulphate (50 gm) and distilled out completely under reduced pressure below 40° C. The residue was stirred with 2 volumes of n-Hexane at 40-45° C., cooled slowly to 0-5° C., the solids filtered, washed with n-Hexane (250 ml) and dried at 40-45° C. to yield the title compound (638 gm, 92% yield).

EXAMPLE 7

Preparation of 5-nitro isovanillin (Formula II)

Isovanillin (500 gm) and acetic acid (1750 ml) were cooled to −5 to 0° C. To this solution, nitric acid (750 ml) was charged slowly at −5 to 0° C. with stirring. The temperature of the reaction mass was slowly raised to 25-30° C. and maintained for 12 hours. The reaction mass was quenched into ice water (4 kg), the solids filtered and washed with water (2 lt). The solids were stirred with a 1% sodium bicarbonate solution (1 lt), filtered and dried at 45-50° C. The solid was dissolved in 6 volumes of ethyl acetate, ethyl acetate was distilled off up to half the volume and 3 volumes of n-Hexane were charged slowly at 45-50° C. The reaction mass was cooled slowly to 0-5° C., maintained for 1 hour, the solids filtered, washed with 0.5 volumes of 1:1 mixture of ethyl acetate:n-Hexane and dried at 45-50° C. to yield the title compound (423 gm, 65% yield).

EXAMPLE 8

Preparation of Methyl-2-hydroxy-3-methoxy benzoate (Formula VIII)

a) Preparation of 3-hydroxy-4-methoxy benzoic acid

Methanol (350 ml), isovanillin (50 gm) and 30% methanolic sodium hydroxide solution (1 ml), were heated to 45° C. To this solution, 35% hydrogen peroxide solution (107 ml) was charged slowly maintaining pH at 10.5 to 11.5 using methanolic sodium hydroxide solution over a period of 2-3 hours. The reaction mass was quenched into chilled water (1 lt) and the pH adjusted to 2-3 using hydrochloric acid. The solids were filtered, washed with 50% aqueous methanol (50 ml) and dried at 45-50° C. to yield 3-hydroxy-4-methoxy benzoic acid.

b) Preparation of Methyl-2-hydroxy-3-methoxy benzoate

The solid obtained in step a), was refluxed with 10% methanolic hydrochloric acid solution (250 ml) for 6 hours. The reaction mass was quenched into chilled water (1 lt) and repeatedly extracted with methylene chloride (250 ml). The combined methylene chloride layer was washed with water (100 ml×2) and methylene chloride distilled out completely at 35-40° C. The residue was stirred in hexane (1.50 ml), at 25-30° C. The solid obtained was filtered, washed with: hexane (25 ml) and dried at 40-45° C. to yield the title compound (50 gm, 83% yield).

EXAMPLE 9

Preparation of Methyl-5-hydroxy-4-methoxy-2-nitro benzoate (Formula IX)

Methyl-2-hydroxy-3-methoxy benzoate (50 gm) and acetic acid (175 ml) were cooled to 0-5° C. To this solution, 70% nitric acid solution (75 ml) was charged slowly at 0-5° C. under stirring and the reaction mass was further stirred for 18 hours. The reaction mass was quenched into chilled water (800 ml) and extracted repeatedly with methylene chloride (400 ml). The combined methylene chloride layer was washed with water, followed by 1% potassium carbonate solution (100 ml), dried over sodium sulphate and methylene chloride distilled off completely at 35-40° C. The residue was dissolved in 10% aqueous methanol (250 ml). The filtrate was gradually cooled to 0-5° C. and maintained for 1 hour. The solid obtained was filtered, washed with 10% aqueous methanol (100 ml) and dried at 40-45° C. to yield the title compound (46 gm, 74% yield).

EXAMPLE 10

Preparation of Methyl-2-amino-5-hydroxy-4-methoxy benzoate (X)

Ethyl acetate (300 ml), methyl-5-hydroxy-4-methoxy-2-nitro benzoate (50 gm) and 10% palladium/carbon (5 gm) were hydrogenated under a hydrogen gas pressure of 5-6 kg for 4 hours. The reaction mass was filtered to remove catalyst. The filtrate was distilled off to remove solvent. The residue obtained was stirred in n-hexane (100 ml) at 0-5° C. The solid obtained was filtered and washed with n-hexane (25 ml) to yield the title compound (40 gm, 93% yield).

EXAMPLE 11

Preparation of 6-hydroxy-7-methoxy-quinazoline-4-one (formula XI)

Methyl-2-amino-5-hydroxy-4-methoxy benzoate (50 gm), methanol (400 ml) and formamidine acetate (30 gm) were refluxed for 10 hours. The reaction mass was gradually cooled to 5-10° C. and stirred for 1 hour. The solid obtained was filtered and washed with methanol (150 ml) and dried at 50-55° C. to yield the title compound (45 gm, 92% yield).

The invention claimed is:
1. A process for preparing gefitinib of formula I

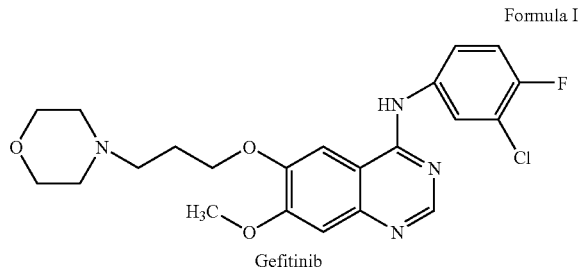 [SMILES: COc1cc2ncnc(Nc3ccc(F)c(Cl)c3)c2cc1OCCCN1CCOCC1]

Formula I

Gefitinib comprising:
converting a compound of formula III

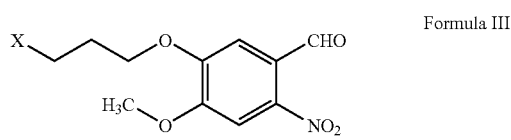

Formula III to a compound of formula V,

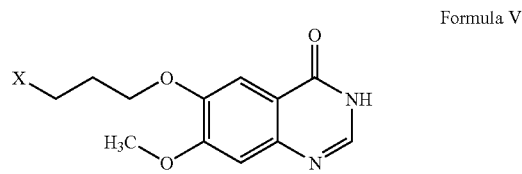

Formula V and converting the compound of formula V to gefitinib, wherein the conversion of the compound of formula V comprises chlorinating the compound of formula V to produce a compound of formula VI

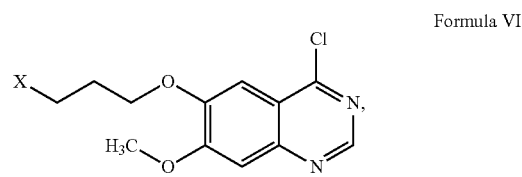

Formula VI and wherein X is fluoro, chloro, bromo or iodo.

2. The process according to claim 1, wherein the conversion to gefitinib further comprises reacting the compound of formula VI with morpholine to produce the compound of formula VII

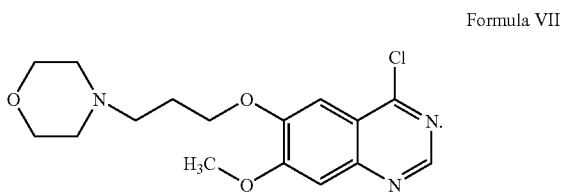 [SMILES: COc1cc2ncnc(Cl)c2cc1OCCCN1CCOCC1]

Formula VII

3. The process according to claim 2, wherein the conversion to gefitinib further comprises condensing the compound of formula VII with 3-chloro-4-fluoroaniline.

4. The process according to claim 1, further comprising converting a compound of formula II

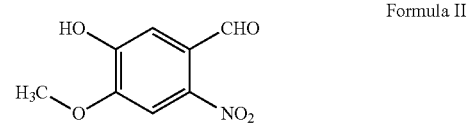

Formula II to the compound of formula III.

5. The process according to claim 4, wherein the conversion comprises reacting the compound of formula II with a compound of formula $X(CH_2)_3X$, wherein each X is independently selected from fluoro, chloro, bromo or iodo.

6. The process according to claim 4, wherein the conversion of the compound of formula II is carried out in the presence of acetonitrile and $K_2CO_3$.

7. The process according to claim 4, wherein the compound of formula II is prepared by nitrating isovanillin.

8. The process according to claim 1, wherein the compound of formula III is converted to the compound of formula V via the intermediate compound of formula IV

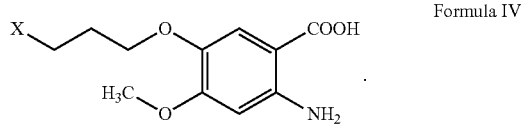

Formula IV

9. The process according to claim 8, wherein the compound of formula III is converted to the compound of formula IV by oxidation followed by reduction.

10. The process according to claim 9, wherein the oxidation comprises reacting the compound of formula III with a base and a peroxide.

11. The process according to claim 10, wherein the base is an alcoholic NaOH solution.

12. The process according to claim 10, wherein the peroxide is $H_2O_2$.

13. The process according to claim 9, wherein the reduction comprises hydrogenation in the presence of a noble metal catalyst.

14. The process according to claim 13, wherein the source of hydrogen is hydrogen gas or a hydrogen-donating compound, and wherein the hydrogenation is carried out in a solvent comprising ethyl acetate.

15. The process according to claim 8, wherein the compound of formula IV is converted to the compound of formula V by the Niementowski synthesis, and wherein the conversion of the compound of formula IV to the compound of formula V comprises reaction of the compound of formula IV with $HCONH_2$ and ammonium formate.

16. The process according to claim 1, wherein X is chloro or bromo.

17. The process according to claim 1, wherein X is chloro.

18. The process according to claim 5, wherein one of the X goups is chloro and the other X group is bromo.

19. The process according to claim 10, wherein the base is a methanoic NaOH solution.

20. The process according to claim 9, wherein the reduction comprises hydrogenation in the presence of palladium.

\* \* \* \* \*

UNITED STATES PATENT AND TRADEMARK OFFICE
CERTIFICATE OF CORRECTION

PATENT NO. : 8,350,029 B2  Page 1 of 1
APPLICATION NO. : 12/595812
DATED : January 8, 2013
INVENTOR(S) : Rao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 364 days.

Signed and Sealed this
First Day of September, 2015

Michelle K. Lee
*Director of the United States Patent and Trademark Office*